(12) United States Patent
Fontaine et al.

(10) Patent No.: US 8,357,105 B2
(45) Date of Patent: Jan. 22, 2013

(54) ANTI-REFLUX MECHANISM FOR URINE COLLECTION SYSTEMS

(75) Inventors: Chelsey Fontaine, Needham, MA (US);
Stephen Tully, Quincy, MA (US);
Lawrence Salvadori, San Diego, CA (US)

(73) Assignee: Covidien LP, Mansfield, MA (US)

( * ) Notice: Subject to any disclaimer, the term of this patent is extended or adjusted under 35 U.S.C. 154(b) by 383 days.

(21) Appl. No.: 12/187,620

(22) Filed: Aug. 7, 2008

(65) Prior Publication Data

US 2010/0036283 A1 Feb. 11, 2010

(51) Int. Cl.
*A61B 5/00* (2006.01)

(52) U.S. Cl. ........................................................ 600/580

(58) Field of Classification Search .................. 128/275;
150/12; 220/9.1, 477; 248/95; 600/573,
600/580, 581, 586, 575, 584; 604/317, 318,
604/319, 322, 323, 324, 325, 347; 73/273;
137/40, 43, 44, 98, 577
See application file for complete search history.

(56) References Cited

U.S. PATENT DOCUMENTS

| | | | |
|---|---|---|---|
| 616,336 A * | 12/1898 | Kersten | 210/172.2 |
| 3,650,272 A | 3/1972 | Ericson | |
| 3,651,810 A | 3/1972 | Ormerrod | |
| 3,683,894 A * | 8/1972 | Villari | 600/580 |
| 3,740,770 A | 6/1973 | Villari | |
| 3,776,231 A * | 12/1973 | Holbrook et al. | 604/322 |
| 3,831,453 A | 8/1974 | McWhorter et al. | |
| 3,888,126 A | 6/1975 | Cross | |
| 3,897,785 A | 8/1975 | Barto | |
| 3,931,650 A | 1/1976 | Miller | |
| 3,961,529 A | 6/1976 | Hanifl | |
| 3,965,900 A | 6/1976 | Boedecker | |
| 3,967,645 A | 7/1976 | Gregory | |
| D242,653 S | 12/1976 | Ekbladh et al. | |
| 4,000,649 A | 1/1977 | Hanifl | |
| 4,002,075 A | 1/1977 | Cross | |
| 4,073,295 A | 2/1978 | Laufbaun | |
| 4,084,589 A | 4/1978 | Kulvi | |
| 4,095,589 A | 6/1978 | Manschot et al. | |
| 4,178,934 A | 12/1979 | Forman | |
| 4,189,789 A | 2/1980 | Hofstetter | |
| 4,254,771 A | 3/1981 | Vidal | |
| RE30,607 E | 5/1981 | Manschot et al. | |
| 4,301,813 A | 11/1981 | Merry et al. | |

(Continued)

FOREIGN PATENT DOCUMENTS

WO    WO 00/18298    4/2000

*Primary Examiner* — Max Hindenburg
(74) *Attorney, Agent, or Firm* — Lisa E. Winsor, Esq.

(57) ABSTRACT

A urine collection system includes an anti-flux mechanism to reduce the amount of urine that may flow from within the collection bag back into the urine meter. The urine collection system includes a urine meter, a collection member defining at least a first opening for receiving urine from the urine meter and a shield positioned adjacent the opening of the collection member. The shield is affixed to the collection member at predetermined connection points along a periphery of the shield whereby urine flows between the connection points from the urine meter to the collection member. The shield may be affixed to an internal surface of the bag. The shield may be spot welded to the collection member at the connection points. The shield may include at least a first slot configured to permit the passage of fluid therethrough.

10 Claims, 9 Drawing Sheets

U.S. PATENT DOCUMENTS

| | | |
|---|---|---|
| 4,305,290 A | 12/1981 | Taylor |
| 4,305,404 A | 12/1981 | Dunn |
| 4,305,405 A | 12/1981 | Meisch |
| 4,483,688 A | 11/1984 | Akiyama |
| 4,564,361 A | 1/1986 | Akiyama |
| 4,579,126 A | 4/1986 | Cianci |
| 4,615,692 A | 10/1986 | Giacalone et al. |
| 4,622,981 A | 11/1986 | Sherlock |
| 4,625,734 A * | 12/1986 | Sherlock et al. ............ 600/575 |
| 4,633,887 A | 1/1987 | Edwards et al. |
| 4,699,155 A | 10/1987 | Villari et al. |
| 4,728,324 A | 3/1988 | Steigerwald et al. |
| 4,731,062 A | 3/1988 | Gross et al. |
| 4,736,925 A | 4/1988 | Kamstrup-Larsen et al. |
| 4,743,236 A | 5/1988 | Manschot |
| D296,360 S | 6/1988 | Oelberg |
| 4,790,837 A | 12/1988 | Gross et al. |
| 4,804,376 A | 2/1989 | Layton |
| 4,815,477 A | 3/1989 | McWhorter et al. |
| 4,827,944 A | 5/1989 | Nugent |
| 4,838,883 A | 6/1989 | Matsuura |
| 4,850,375 A | 7/1989 | Rosenberg |
| D303,714 S | 9/1989 | Manschot |
| 4,886,510 A | 12/1989 | Matsuura |
| 4,913,161 A | 4/1990 | Villari et al. |
| 5,053,027 A | 10/1991 | Manfredi |
| 5,112,324 A | 5/1992 | Wallace |
| 5,119,675 A | 6/1992 | Mohiuddin |
| 5,135,199 A | 8/1992 | Cross et al. |
| 5,295,397 A * | 3/1994 | Hall et al. ............... 73/861.02 |
| 5,397,315 A | 3/1995 | Schmidt et al. |
| 5,409,014 A | 4/1995 | Napoli et al. |
| 5,429,624 A | 7/1995 | Coelho |
| 5,460,606 A | 10/1995 | Daneshvar |
| 5,484,428 A * | 1/1996 | Drainville et al. ............ 604/319 |
| 5,496,300 A | 3/1996 | Hirsch et al. |
| D395,356 S | 6/1998 | Tang |
| 5,769,087 A * | 6/1998 | Westphal et al. ............ 600/573 |
| 5,776,077 A | 7/1998 | Kottig |
| 5,792,042 A | 8/1998 | Cohen et al. |
| 5,865,821 A | 2/1999 | Lowey |
| 6,024,257 A | 2/2000 | Djavit |
| 6,059,761 A | 5/2000 | Tsukada et al. |
| 6,090,087 A | 7/2000 | Tsukada et al. |
| 6,299,598 B1 | 10/2001 | Bander |
| 6,348,046 B2 * | 2/2002 | Voges et al. ............ 604/323 |
| 6,352,526 B1 | 3/2002 | Cawood |
| 6,471,680 B1 | 10/2002 | Cawood |
| D476,079 S | 6/2003 | Kubalak et al. |
| 6,716,200 B2 | 4/2004 | Bracken et al. |
| 6,722,319 B1 | 4/2004 | Chiu |
| D496,099 S | 9/2004 | Bisbee |
| D496,727 S | 9/2004 | Kubalak et al. |
| D496,993 S | 10/2004 | Kubalak et al. |
| D497,205 S | 10/2004 | Kubalak et al. |
| 6,887,223 B2 | 5/2005 | Bisbee |
| 6,887,230 B2 | 5/2005 | Kubalak et al. |
| D508,128 S | 8/2005 | Kubalak et al. |
| 7,001,370 B2 | 2/2006 | Kubalak et al. |
| 7,008,407 B1 | 3/2006 | Kamp |
| 7,150,739 B2 | 12/2006 | O'Neil |
| 7,487,800 B2 * | 2/2009 | Lammers ............ 138/37 |
| 2001/0005782 A1 | 6/2001 | Tanghoj et al. |
| 2002/0077609 A1 | 6/2002 | Johnson |
| 2002/0103460 A1 | 8/2002 | Kubalak et al. |
| 2002/0103467 A1 | 8/2002 | Kubalak |
| 2003/0032944 A1 | 2/2003 | Cawood |
| 2003/0130646 A1 | 7/2003 | Kubalak et al. |
| 2003/0139730 A1 | 7/2003 | Bracken et al. |
| 2004/0171979 A1 | 9/2004 | O'Neil |
| 2004/0204695 A1 | 10/2004 | Bisbee |
| 2004/0230181 A1 | 11/2004 | Cawood |
| 2006/0015082 A1 | 1/2006 | Pearson et al. |
| 2006/0100743 A1 | 5/2006 | Townsend et al. |
| 2006/0111681 A1 | 5/2006 | Vernon |
| 2006/0173420 A1 * | 8/2006 | Fangrow ............ 604/247 |
| 2006/0189962 A1 | 8/2006 | Burtoft |
| 2006/0212024 A1 | 9/2006 | Blake |
| 2006/0293631 A1 | 12/2006 | Bolt |
| 2007/0185465 A1 | 8/2007 | Campbell et al. |
| 2007/0203464 A1 * | 8/2007 | Green et al. ............ 604/323 |
| 2007/0203465 A1 | 8/2007 | Salvadori et al. |
| 2007/0213639 A1 | 9/2007 | Salvadori et al. |
| 2007/0225666 A1 | 9/2007 | Otto |
| 2007/0225667 A1 | 9/2007 | Otto |
| 2007/0225668 A1 | 9/2007 | Otto |
| 2007/0260208 A1 | 11/2007 | May |
| 2008/0009813 A1 | 1/2008 | Salvadori et al. |
| 2008/0171966 A1 | 7/2008 | Rudko et al. |
| 2008/0243097 A1 | 10/2008 | Goss |

\* cited by examiner

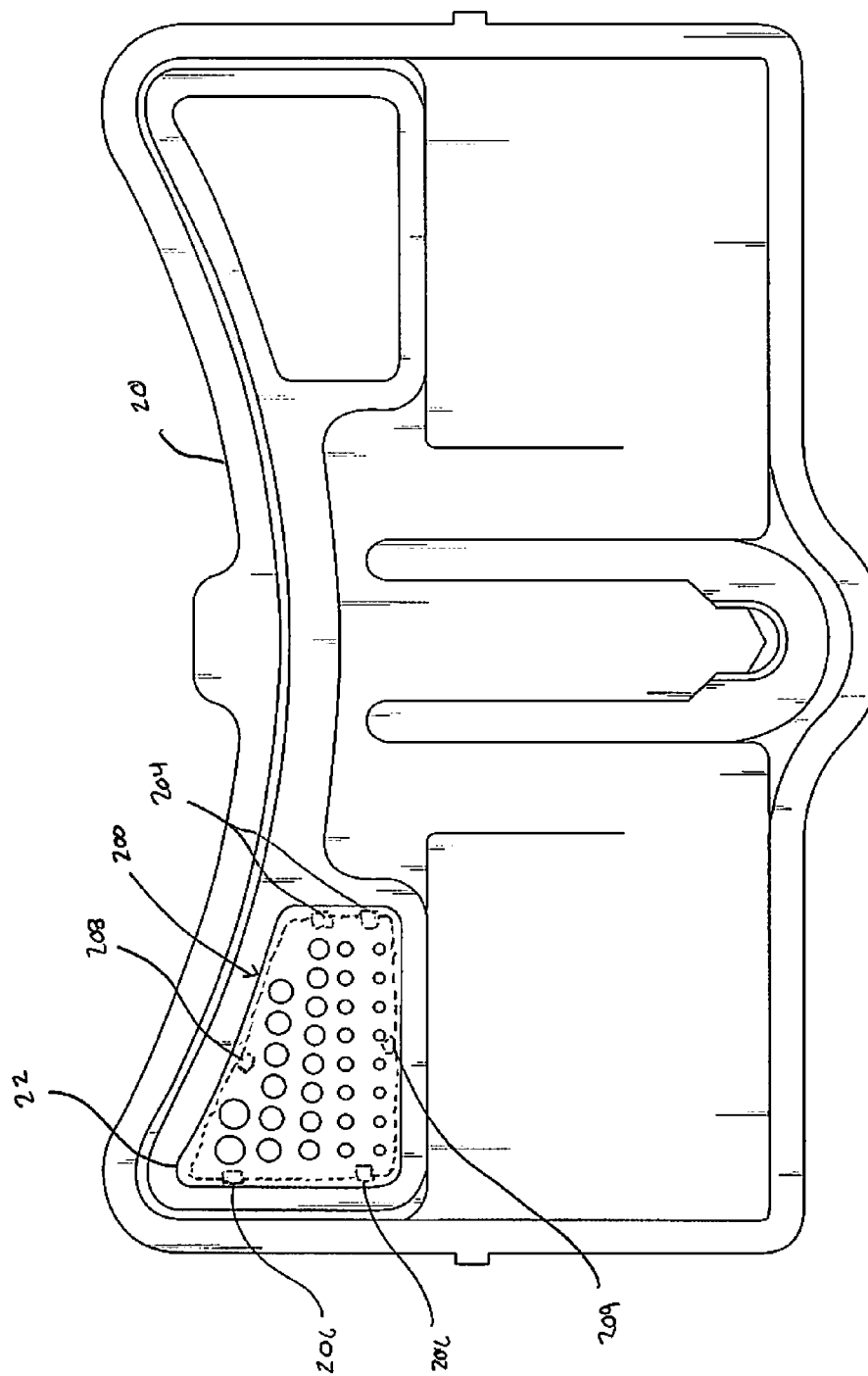

ANTI-REFLUX MECHANISM FOR URINE COLLECTION SYSTEMS

BACKGROUND

1. Technical Field

The present disclosure relates to a urine meter for use with a urine collection bag or system. More specifically, the present disclosure relates to a urine meter constructed to facilitate faster drainage and more precise volume measurement.

2. Background of Related Art

Urine meters are well known and are commonly used in conjunction with urine collection systems for catheterized patients. Typically, a urine meter is secured to a urine collection bag and receives urine from a supply tube which is connected to a catheterized patient. The urine meter has a limited volume and includes indicia for measuring the volume of fluid deposited therein. The urine meter is attached to a urine collection bag of greater volume and includes at least one drain opening positioned in an upper portion of the meter which is in fluid communication with the urine collection bag. After a predetermined period of time of use, the volume of urine in the urine meter can be recorded and the contents of the urine meter can be emptied into the urine collection bag.

SUMMARY

Accordingly, it would desirable to provide a urine collection system that includes an anti-flux mechanism to reduce the amount of urine that may flow from within the collection bag back into the urine meter. In one embodiment, a urine collection system includes a urine meter, a collection member defining at least a first opening for receiving urine from the urine meter and a shield positioned adjacent the opening of the collection member. The shield is affixed to the collection member at predetermined connection points along a periphery of the shield whereby urine flows between the connection points from the urine meter to the collection member. The shield may be affixed to an internal surface of the bag. The shield may be spot welded to the collection member at the connection points. The shield may include at least a first slot configured to permit the passage of fluid therethrough.

In another embodiment, a urine collection system includes a urine meter defining a dump port, a collection member defining an opening for receiving urine from the urine meter and a guard mounted adjacent the dump port of the urine meter. The guard has at least one passage for permitting the passage of urine from the dump port into the opening and into the collection member. The guard may include a plurality of passages for permitting passage of urine. At least some of the passages of the guard may define different internal dimensions. The internal dimensions of the passages of the guard may increase from a lower end of the guard to an upper end of the guard. The passages may be in the form of slots in the guard. A flap may be positioned adjacent the passage of the guard. The flap may be adapted to be displaced relative to the passage to permit passage of urine from the dump port through the opening and into the collection member, and to selectively cover the passage when the urine in the collection member reaches a predetermined level.

In another embodiment, a urine collection system includes a urine meter defining a dump port, a collection member defining at least a first opening for receiving urine from the urine meter, a backboard disposed in the collection member and a flange extending from the backboard and configured to fluidly communicate with the dump port of the urine collection. The backboard may include ribs which define channels therebetween to permit urine to flow. The urine port may define a second dump port and the backboard may include a second flange configured to fluidly communicate with the second dump port. The backboard may define a substantially "T" shaped planar member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serene to explain the principles of the disclosure, wherein:

FIG. 4C is a front view of the anti-reflux mechanism of FIGS. 4A and 4B selectively secured to a urine meter;

DETAILED DESCRIPTION

Figure 1:
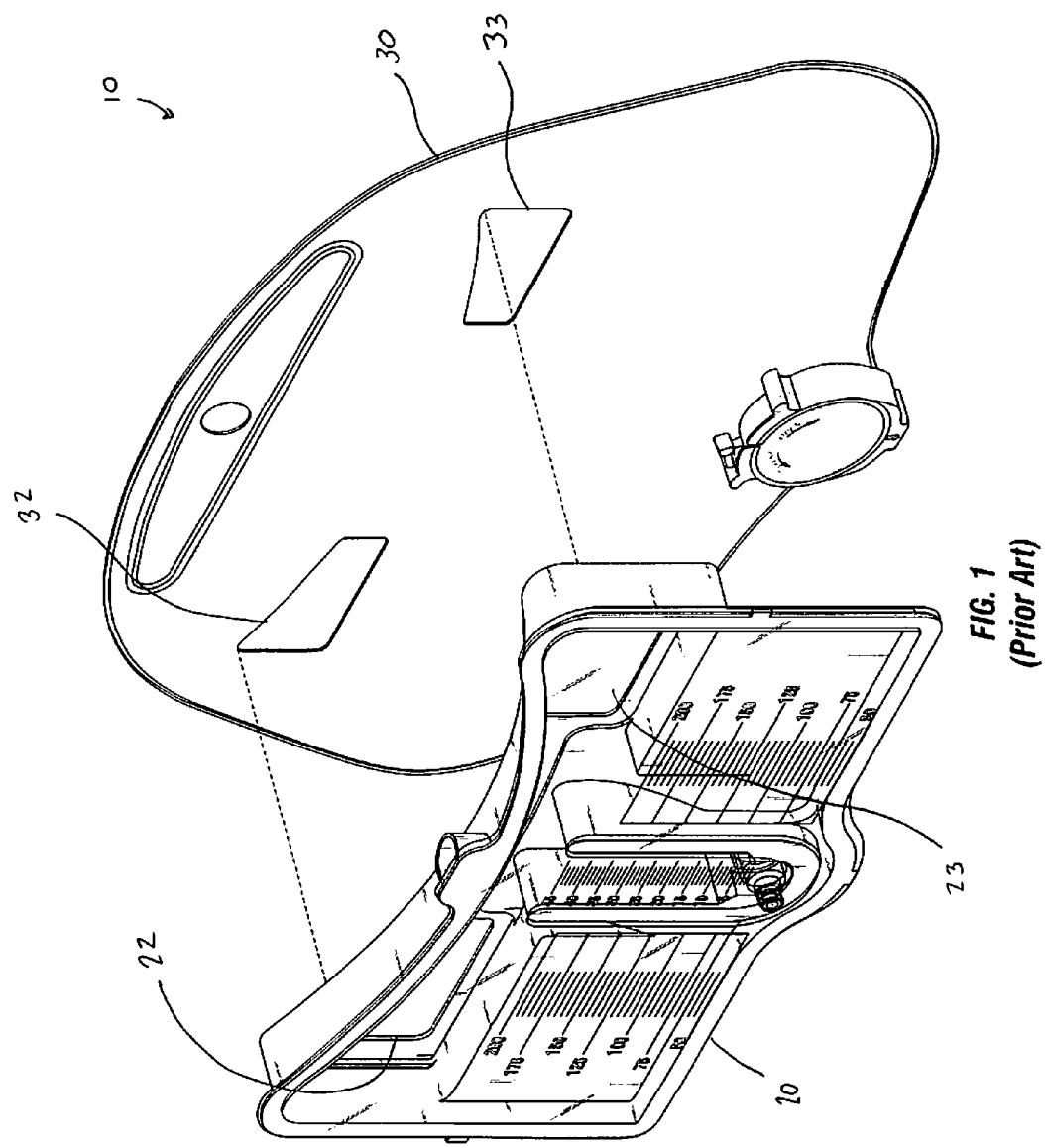
FIG. 1 is a exploded perspective view of a prior art urine collection system including a urine meter and a collection bag.
Figure 2:
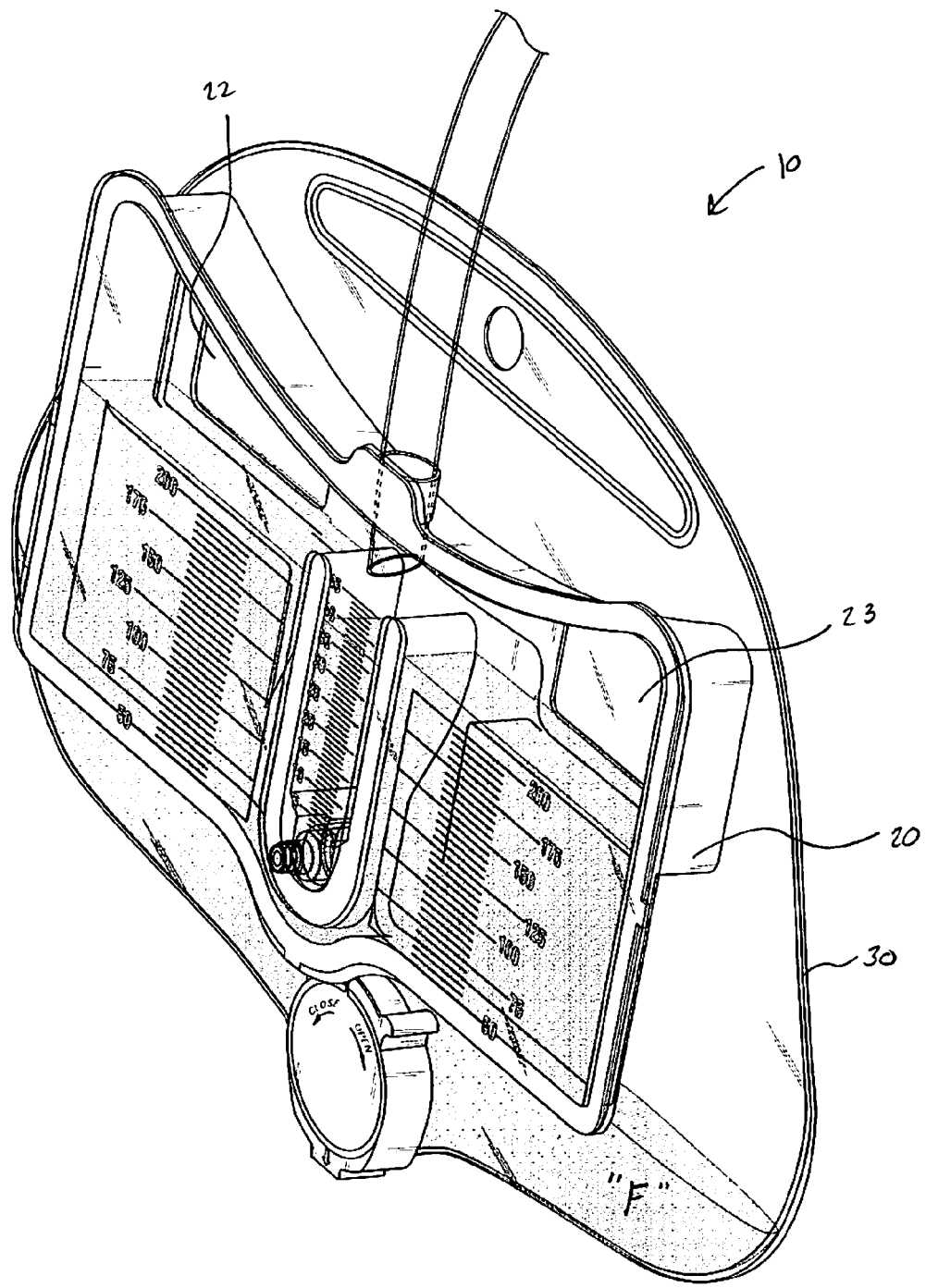
FIG. 2 is a perspective view of the urine collection system of FIG. 1.

Referring initially to FIGS. 1 and 2, a prior art urine collection system is shown generally as urine collection system 10. Urine collection system 10 is described in detail in commonly owned U.S. Patent Application Publication No. 2007/0213639, the contents of which is hereby incorporated by reference in their entirety, and will only be discussed to the extent necessary to enable the aspects of the present disclosure. Urine collection system 10 includes a urine meter 20 and a collection member or bag 30. Urine meter 20 includes two large dump ports 22, 23 which are in fluid communication with openings 32, 33 formed in collection bag 30. Fluid "F" flows into urine meter 20 through tube "T" where the amount of fluid "F" may be measured before urine collection system 10 is tilted and fluid "F" drains into collection bag 30. While the configuration of urine collection system 10 enables a user to easily drain fluid "F" from urine meter 20 into collection bag 30, accident tilting of urine collection system 10 may also cause reflux of fluid "F" from collection bag 30 back into urine meter 20 through dump ports 22, 23.

Figure 3:
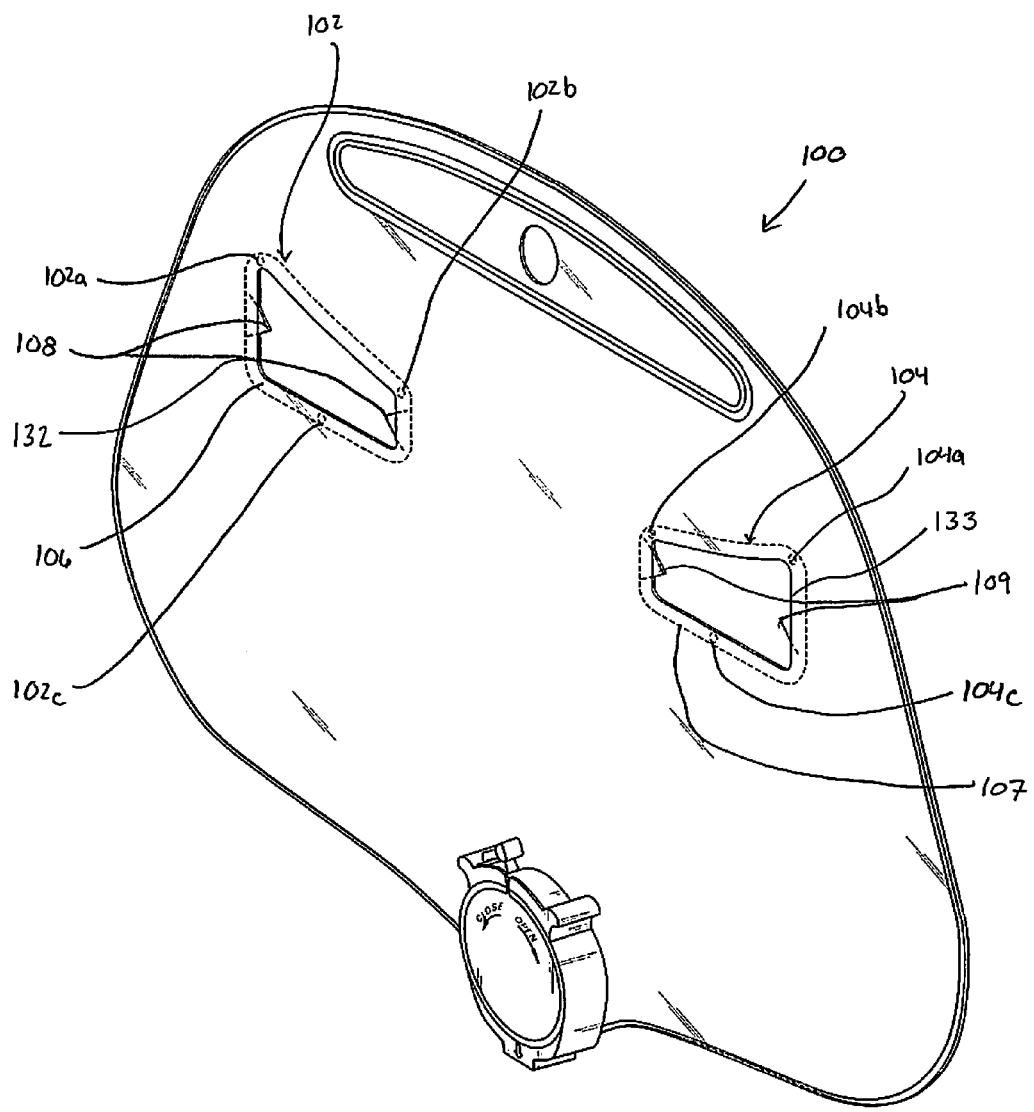
FIG. 3 is a perspective view of one embodiment of an anti-reflux mechanism according to aspects of the present disclosure.

Turning now to FIG. 3, a first embodiment of an anti-reflex mechanism according to the present disclosure is shown generally as shielded collection bag 100. Anti-reflux collection bag 100 is substantially similar to collection bag 30 discussed hereinabove, and will only be described as relates to the differences therebetween. Anti-reflux collection bag 100 defines openings 132, 133 for receiving fluid from a urine meter. Anti-reflux collection bag 100 further includes shields 102, 104 partially obstructing openings 132, 133.

Shields 102, 104 may be constructed of vinyl or other suitable material. Shields 102, 104 are sized and dimensioned to cover openings 132, 133. Shields 102, 104 are affixed to the inner surface of collection bag 100. Shields 102, 104 are positioned within collection bag 100 over openings 132, 133. Once in position, shields 102, 104 are attached to collection bag 100 at select points 102a-c, 104a-c about the perimeter of shields 102, 104, respectively. Shields 102, 104 may be attached to collection bag 100 using spot welding, adhesive or other suitable methods. As shown, shields 102, 104 are each attached to collection bag 100 at three points 102a-c, 104a-c, respectively, however, fewer or more attachment points may be used. It is envisioned that attachment points 102a-c, 104a-c may be positioned at any suitable point along overlapping portions of collection bag 100 and shields 102, 104, respectively. By attaching shields 102, 104 at select attachment points 102a-c, 104a-c, the remaining areas of overlap between collection bag 100 and shields 102, 104, namely overlap portions 106, 107 remain unattached to collection bag 100. In this manner, fluid "F" is permitted to flow from a urine meter, around or between attachment points 102a-c, 104c, and into collection bag 100. Overlap portions 106, 107 may be configured to prevent sticking of shields 102, 104, respectively, to collection bag 100. For example, overlap portions 106, 107 may include knobs, ridges or other suitable configurations (not shown) to prevent shields 102, 104 from sealing to bag 100. Overlap portions 106, 107 may instead or further include a film or coating between shields 102, 104 and collection bag 100 to prevent sticking of overlap portions 106, 107.

Shields 102, 104 further include flaps 108, 109, respectively, configured to permit additional flow of fluid "F" from a urine meter into collection bag 100. Flaps 108, 109 are configured to deflect inwardly from the urine meter as fluid "F" enters collection bag 30 while restricting movement of the flaps 108, 109 in an outward direction toward the urine meter. In this manner, flaps 108, 109 permit more fluid "F" to drain into collection bag 100 than is permitted to reflux back into the urine meter. Flaps 108, 109 may be positioned in any suitable location about shields 102, 104, respectively. Shields 102, 104 may include any number of flaps 108, 109, respectively, including no flaps at all.

Figure 4A:
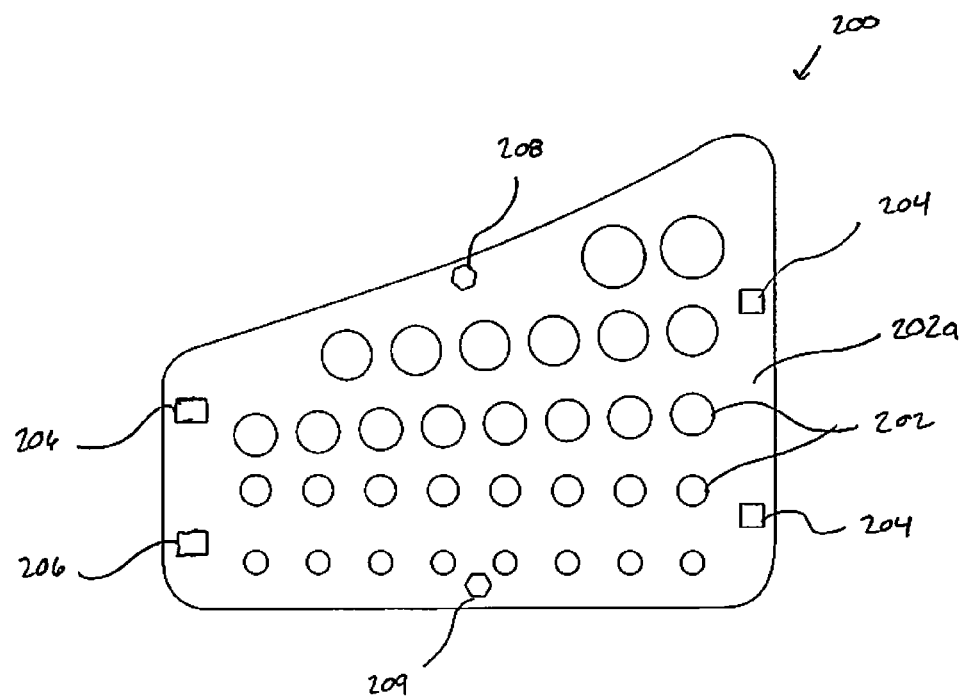
FIGS. 4A and 4B are front and back side views of another embodiment of an anti-reflux mechanism according to aspects of the present disclosure.
Figure 4B:
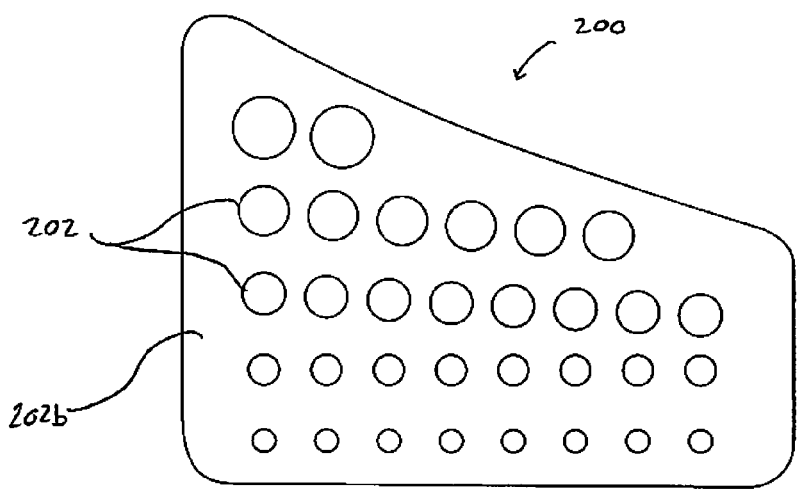

Turning now to FIGS. 4A-C, another embodiment of an anti-reflux mechanism according to the present disclosure is shown generally as anti-reflux guard 200. Anti-reflux guard 200 is configured to be secured within dump port 22 of urine meter 20 (FIG. 1). In this manner, guard 200 would be positioned between urine meter 20 and a collection bag 30 to control the flow of fluid "F" therebetween. A second guard (not shown) is a substantial mirror image of anti-reflux guard 200 and is configured to be secured within dump port 23 of urine meter 20. In addition, openings 202 may be directional valves or one way openings permitting flow only in one direction from the urine meter to collection bag 100.

Guard 200 defines a substantially planar member having a first side 202a and a second side 202b. As will be discussed in further detail below, first side 202a of guard 200 is configured to engage dump port 22 of urine meter 20 (FIG. 1). Guard 200 includes a plurality of horizontally spaced openings 202. Openings 202 define progressively larger internal dimensions or holes from bottom to top. Although shown as circular openings, openings 202 may define any shape. The size and configuration of openings 202 may be varied to control the flow of fluid "F" into collection bag 30 (FIG. 1) and the reflux of fluid "F" back into urine meter 20. The size and configuration of openings 202 may also be varied to control the passing of clots into collection bag 30. In addition, openings 202 may be directional or one way valves or openings permitting flow only in the direction from urine meter 20 to collection bag 100.

Guard 200 may be secured to dump port 22 of urine meter 20 in any suitable manner, including bonding, adhesive and friction or snap-fit. Alternatively, guard 200 may be integrally formed with urine meter 20. As shown, guard 200 is configured to be snap-fit within dump port 22 of urine meter 20. Guard 200 includes snap members 204 and locators 206. Locators 206 are located opposite snap members 204 and are configured to engage a first edge 22a of dump port 22. Snap members 204 are configured to selectively engage a second edge 22b of dump port 22. Guard 200 may include any number of snap members 204 and locators 206. Guard 200 further includes guides 208, 209 configured to align guard 200 within dump port 22. Guides 208, 209 are configured to engage third and fourth edges 22c, 22d, respectively, of dump port 22. Guard 200 may include any number of guides 208, 209. Snap members 204, locators 206 and guides 208, 209 align and maintain guard 200 securely within dump port 22. A seal or sealing substance (not shown) may be placed between guard 200 and urine meter 20 to increase the integrity of the seal therebetween.

Figure 5A:
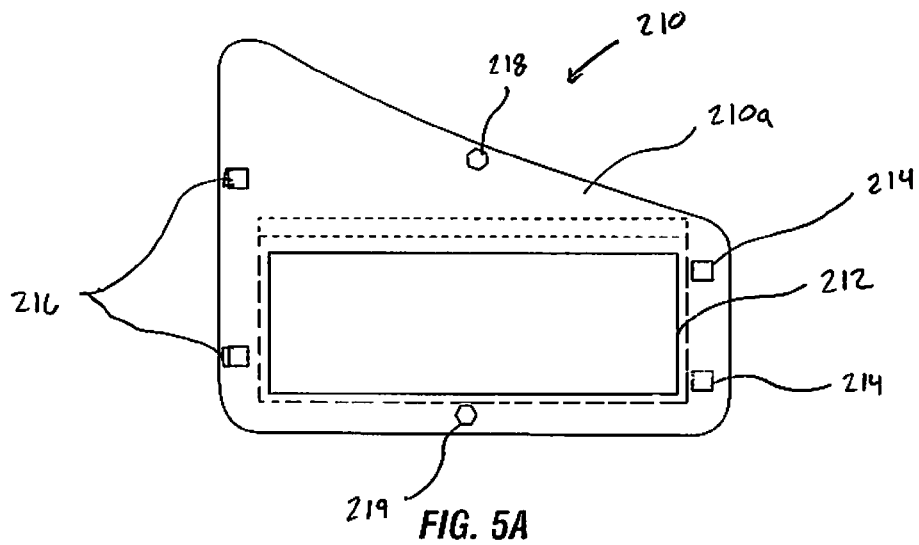
FIGS. 5A and 5B are first and second side view of another embodiment of the anti-reflux mechanism of FIGS. 4A-4C.
Figure 5B:
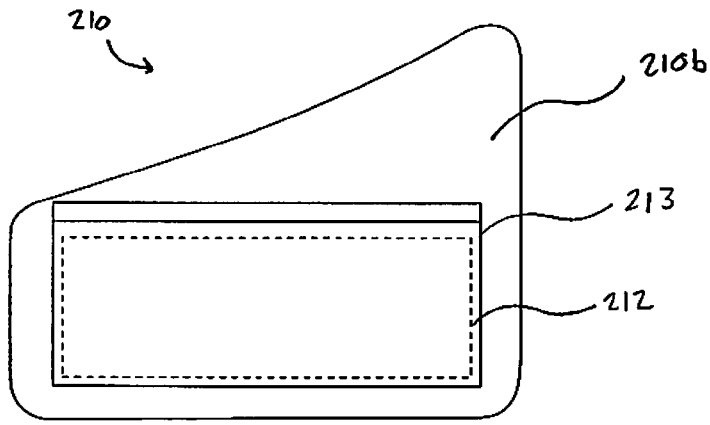
Figure 6:
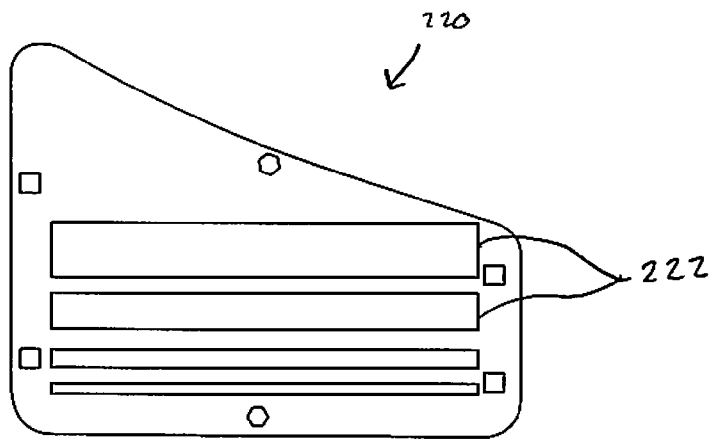
FIG. 6 is a front view of yet another embodiment of the anti-reflux mechanism of FIGS. 4A-4C.
Figure 7A:
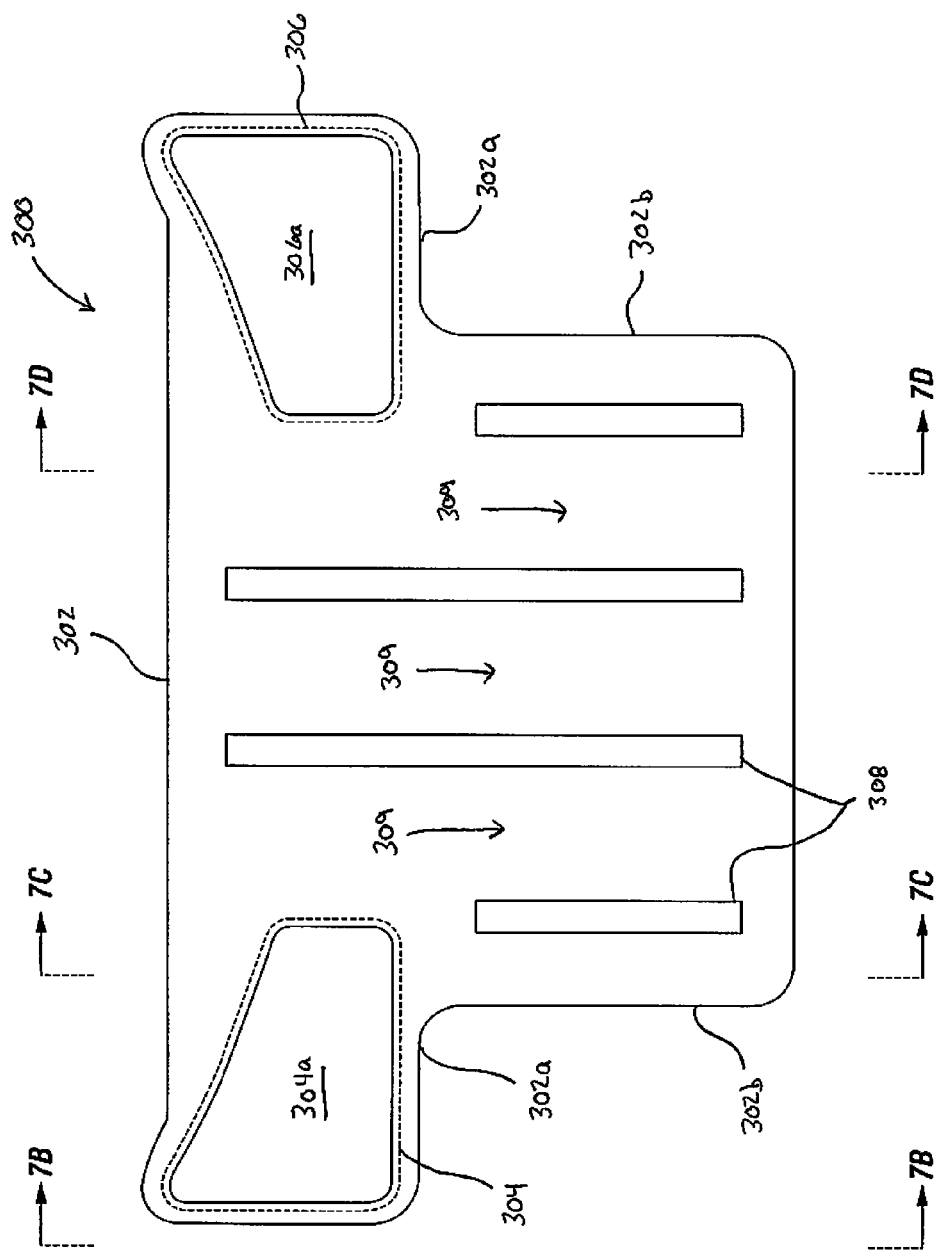
FIG. 7A is a front view of yet another embodiment of an anti-reflux mechanism according to aspects of the present disclosure.
Figure 7D:
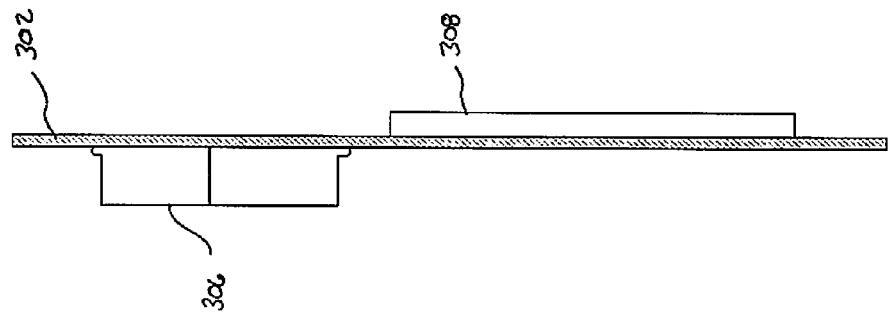
FIGS. 7B-7D are side views of the anti-reflux mechanism of FIG. 7A taken along lines 7B-7B (FIG. 7B), 7C-7C (FIG. 7C), 7D-7D (FIG. 7D)
Figure 7C:
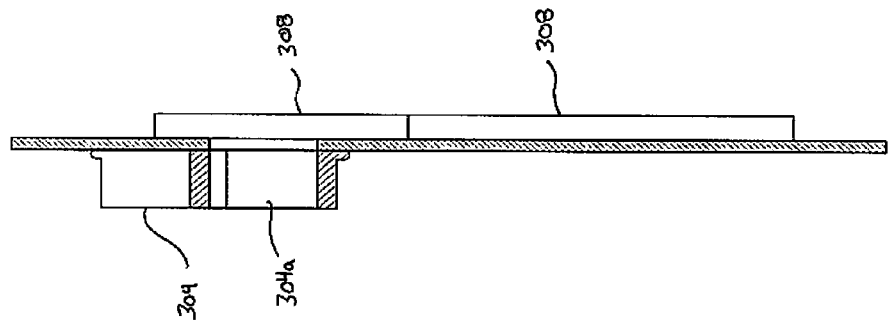
Figure 7B:
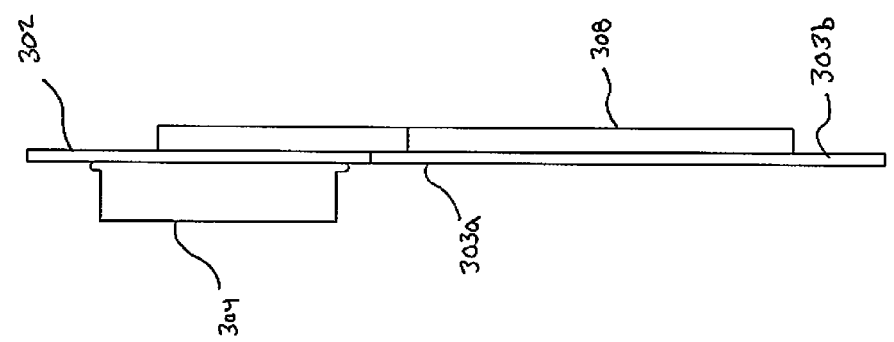
Figure 7E:
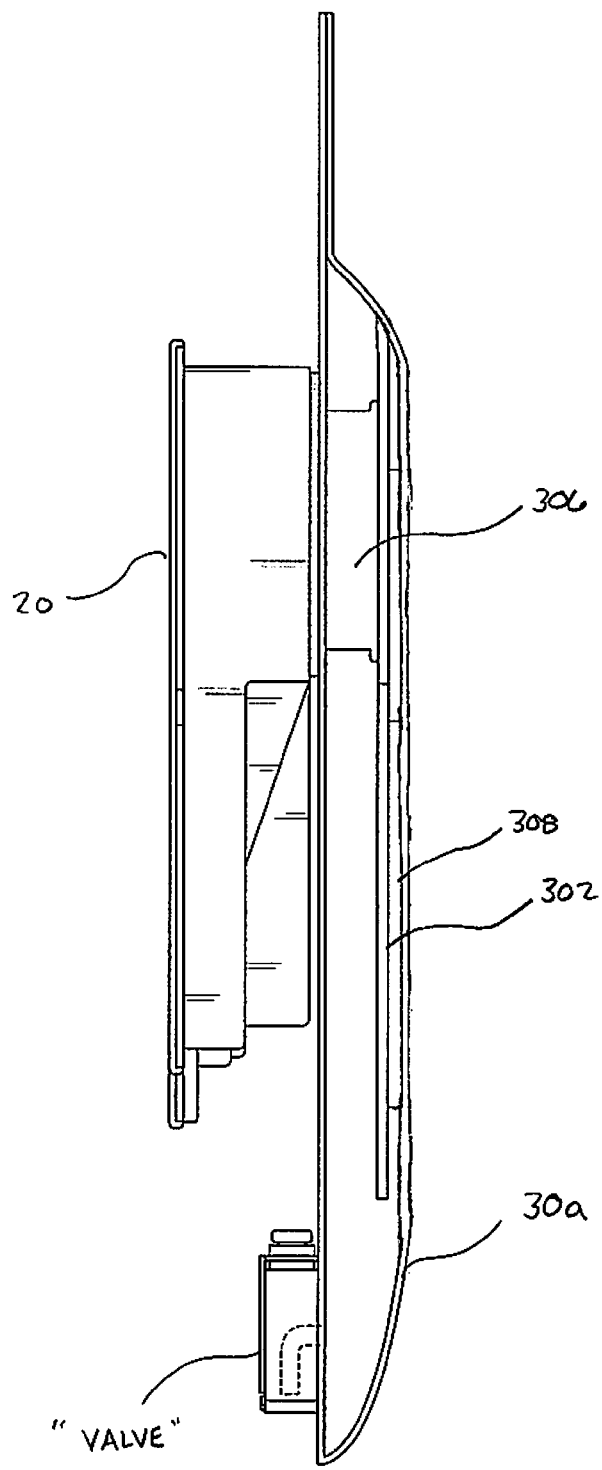
FIG. 7E is a side view of a urine collection system including the anti-reflux mechanism of FIGS. 7A-7D.

Turning now to FIGS. 5A-6, alternate embodiments of anti-reflux guard 200 are shown generally as anti-reflux guards 210, 220. Anti-reflux guards 210, 220 are substantially similar to anti-reflux guard 200, and will only be described in detail as relates to the differences therebetween.

Anti-reflux guard 210 includes first and second sides 210a, 210b and defines a single large opening 212. Opening 212 is covered by a flap 213. Flap 213 is hingedly mounted to second side 210b of guard 210 above opening 212. Flap 213 is sized and dimensioned to extend beyond opening 212. Guard 210 further includes snap members 214, locators 216 and guides 218, 219 configured to retain guard 210 within dump port 23 of urine meter 20 (FIG. 4C). When installed, flap 213 of guard 210 operates to permit the flow of fluid "F" through opening 212 into collection bag 30 (FIG. 1) and prevent the flow, or reflux, of fluid "F" back into urine meter 20. As fluid "F" accumulates within urine meter 20 and encounters opening 212, flap 213 swings away, thereby permitting fluid "F" to enter collection bag 30. As fluid "F" reaches a predetermined level in collection bag 20, the urine contacts the flap 213, in effect, closing the flap 213 by biasing the flap edges extending beyond opening 212 against guard 200. In this manner, fluid "F" is prevent from flowing back into urine meter 20 once it has been drained into collection bag 30 (FIG. 1).

Anti-reflux guard 220 includes horizontal slots 222 that get progressively taller from bottom to top. The size and configuration of horizontal slots 222 may be varied to control the flow of fluid "F" into collection bag 30 (FIG. 1) and the reflux of fluid "F" back into urine meter 20. The size and configuration of horizontal slots 222 may also be varied to control the passing of clots into collection bag 30.

With reference now to FIGS. 7A-E, yet another embodiment of an anti-reflux mechanism according to the present disclosure is shown generally as collection bag insert 300. Insert 300 is configured to be received within a collection bag 30a. Collection bag 30a and insert 300 are configured for use with urine meter 20 and other suitable urine meters. It is envisioned that insert 300 may be modified for use with urine meters of alternative configurations, including urine meters with only a single dump port.

Insert 300 includes backboard 302 and a pair of flanges 304, 306 extending from a first surface 303a of backboard 302. Flanges 304, 306 may be integrally formed with backboard 302, or instead may be fixedly secured to backboard 302 using adhesive, boding or other suitable technique. Backboard 302 defines a substantially planar base having a generally "T" shaped configuration. Flanges 304, 306 are located on a horizontal portion 302a of backboard 302 and define openings 304a, 306a. Flanges 304, 306 are configured to engage dump ports 22, 23, respectively, of urine meter 20. Insert 300 further includes ribs 308 formed on a second surface 303b of backboard 302 and extending along vertical portion 302b thereof. As will be discussed below, when insert 300 is received with collection bag 30a, ribs 308 form channels 309 between backboard 302 and collection bag 30a.

In use, collection bag 30a, including insert 300 is secured to urine meter 20 by any suitable method. Flanges 304, 306 may be configured to extend from collection bag 30a and be received with dump ports 22, 23 (FIG. 1), respectively, of urine meter 20. Alternatively, flanges 304, 306 may be configured to be positioned flush against dump ports 22, 23, respectively, of urine meter 20. Once collection bag 30a is secured to urine meter 20, fluid "F" (FIG. 2) may drain from urine meter 20 into collection bag 30a. Fluid "F" drains out of dump ports 22, 23 of urine meter 20 into openings 304a, 306a of flanges 304, 306. Fluid "F" drains from openings 304a, 306a between second side 303b of backboard 302 and collection bag 30 through channels 309 formed by ribs 308. The configuration of insert 300 reduces the amount of fluid "F" that may reflux back into urine meter 20.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A urine collection system, which comprises:
   a urine meter having a volume to accommodate urine therein;
   a collection member connected to the urine meter and defining at least a first opening for receiving urine from the urine meter; and
   a shield covering the at least first opening of the collection member and being permanently affixed to the collection member at predetermined connection points along a periphery of the shield such that urine must flow between the connection points to pass from the urine meter to the collection member.

2. The urine collection system according to claim 1 wherein the shield is affixed to an internal surface of the collection member.

3. The urine collection system according to claim 1 wherein the shield is spot welded to the collection member at the connection points.

4. The urine collection system according to claim 1, further including a flap disposed between the shield and the collection member.

5. The urine collection system according to claim 4, wherein the flap is configured to deflect towards the collection member as urine flows from the urine meter to the collection member.

6. The urine collection system according to claim 1, wherein the urine meter is configured to be tilted to effect urine drainage from the urine meter to the collection member.

7. A urine collection system, which comprises:
   a urine meter having a volume to accommodate urine therein, the urine meter defining a dump port;
   a collection member connected to the urine meter and defining an opening for receiving urine from the urine meter; and
   a guard covering the dump port of the urine meter, the guard having a plurality of passages formed through the guard which communicate the dump port with the opening in the collection member to allow passage of urine from the urine meter into the collection member, wherein the plurality of passages control the flow of fluid into the collection member and control the reflux of the fluid from the collection member into the urine meter.

8. The urine collection system according to claim 7 wherein at least some of the passages of the guard define different internal dimensions.

9. The urine collection system according to claim 8 wherein the internal dimensions of the passages of the guard increase from a lower end of the guard to an upper end of the guard.

10. The urine collection system according to claim 8 wherein the plurality of passages of the guard define a plurality of slots.

* * * * *